United States Patent
Kohls (10) Patent No.: US 6,763,260 B2
(45) Date of Patent: Jul. 13, 2004

(54) SYSTEM FOR ACQUIRING A PLURALITY OF IMAGES OF A PATIENT AND A CONTROLLER FOR OPERATING THE SAME

(75) Inventor: Mark Kohls, New Berlin, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 365 days.

(21) Appl. No.: 09/682,681

(22) Filed: Oct. 5, 2001

(65) Prior Publication Data

US 2003/0069498 A1 Apr. 10, 2003

(51) Int. Cl.[7] .............................................. A61B 6/00
(52) U.S. Cl. ...................................................... 600/431
(58) Field of Search ............................... 600/407–472; 606/130; 901/1, 2, 8, 6; 128/922, 898, 916; 424/9.51–9.53; 382/62, 128, 153, 194, 195, 294; 378/4, 62, 205, 95

(56) References Cited

U.S. PATENT DOCUMENTS

| | | | |
|---|---|---|---|
| 4,477,923 A | * | 10/1984 | Baumann et al. ............. 378/95 |
| 4,657,756 A | * | 4/1987 | Rasor et al. ................ 424/9.52 |
| 4,917,085 A | * | 4/1990 | Smith ......................... 606/159 |
| 6,240,311 B1 | | 5/2001 | Prince |
| 6,408,201 B1 | | 6/2002 | Foo et al. |

* cited by examiner

Primary Examiner—Ali Imam
(74) Attorney, Agent, or Firm—Michael Best & Friedrich LLP (57) ABSTRACT

A system for acquiring a plurality of internal images of a patient. The system includes a housing connectable to a medium movement sensor. The medium movement sensor generates a movement signal regarding a movement of the medium. The housing is also connectable to an imaging device. The imaging device acquires the internal images upon receiving a control signal having an acquire output. The system further includes a controller secured to the housing. The controller is operable to receive the movement signal, to generate a control signal having an acquire output based on the movement signal, and to provide the control signal having an acquire output to the imaging device.

76 Claims, 3 Drawing Sheets

SYSTEM FOR ACQUIRING A PLURALITY OF IMAGES OF A PATIENT AND A CONTROLLER FOR OPERATING THE SAME

BACKGROUND OF INVENTION

The invention relates to a system for acquiring a plurality of images of a patient, and particularly an image-acquisition system having a controller that receives a monitoring signal and generates an "acquire" output based in part on the monitoring signal.

During a catheterization laboratory procedure (also referred to as a cath-lab procedure), a contrast medium, such as a radio-opaque dye, is injected via a catheter into the patient. For example, the dye may be injected within the patient's heart during an angiograph procedure. When acquiring an image of the area of interest, the dye is used to increase the contrast of the acquired image. The clinician (e.g., the doctor) can then more easily spot plaque blockages or evaluate anatomy (e.g., heart) function.

At the start of the cath-lab procedure, a catheter is typically inserted through an incision, and then fed through an artery up to the area of interest. During the preparation process, an imaging system, such as a x-ray system, uses low-dose radiation for producing low-quality images. The low-quality images are used to guide the catheter to the area of interest. This low-quality image mode is typically referred to as "fluoro mode," and limits the amount of radiation to which the patient is exposed.

Once the catheter is properly positioned, a contrast medium injector (e.g., the dye injector) injects the contrast medium (e.g., the radio-opaque dye) into the area of interest. For prior procedures, an operator (e.g., a doctor, nurse, technician, etc.) manually enters an input to the imaging system during the injection. The manual input changes the state of the imaging system from the fluoro mode to an acquisition mode (also referred to as "cine mode"). During the acquisition mode, the imaging system uses high-dose radiation for acquiring high-resolution images of the area of interest. The high-resolution images are used for analysis by the clinician.

SUMMARY OF INVENTION

For analog systems, the images are acquired with a 35-mm movie film. Typically, the analog system acquires several seconds of frames at a rate of thirty frames per second (fps). Depending on the patient and the number of areas of interest, a clinician may acquire over two-thousand frames per case. For prior systems, because the operator is starting the acquisition mode by entering a manual input, the acquisition period (i.e., the period when the imaging system is in high-resolution mode) is typically unduly long. For example, the operator typically starts the acquisition mode while the catheter is filing with the contrast medium. This guarantees that the acquisition period (also referred to as the "loop") begins before the contrast medium diffuses through the area of interest. Further, the operator typically ends the loop after the contrast medium is too diluted in the area of interest to generate a useful image. This guarantees that the contrast medium has completely run its course. The excessively long acquisition period results in excessive radiation exposure for the patient and staff. Additionally, tube life is reduced since the excessively long acquisition mode is more taxing on the radiation or imaging tube of the imaging system than it really needs to be.

Additionally, an increasing number of imaging systems are acquiring the images using digital acquisition systems, and are storing the acquired digital images on magnetic or optical media. At the time this patent was applied for, current digital imaging systems may use a resolution of 1,024 pixels×1,024 pixels×16 bits/pixels, or two megabytes per frame. For a two thousand frame case, the above resolution results in an image file of four gigabytes of data. While storage devices and networks are continuously increasing in capacity, storing and transmitting multiple image sets of this size is still a challenge for existing technologies.

Accordingly, it would be beneficial to provide a system that optimizes the acquisition period or loop. Optimizing the acquisition period reduces the amount of radiation exposure the patient and staff receive, increases tube life, and reduces the image-set file size. At several loops per case, the reduced exposure, increased tube life and reduced image file size quickly add up for significant benefits. Of course, the optimization period may vary with each loop. Considerations used for optimizing the acquisition period may include, but are not limited to, when the contrast medium is injected within the area of interest, the size of the area of interest, the amount of contrast medium injected, the demographics of the patient (e.g, heart rate, blood pressure, etc.), and similar considerations.

In one embodiment, the invention provides a system for acquiring a plurality of internal images of a patient. The system includes a contrast medium injector operable to introduce a contrast medium within the patient and to generate a movement signal regarding a movement of the medium, and a controller in communication with the injector. The controller is operable to receive the movement signal and to generate a control signal having an acquire output based on the movement signal. The image-acquisition system further includes an imaging system having an imaging device that acquires internal images of the patient. The imaging system is operable to receive the control signal and acquire the plurality of images in response to receiving the acquire output.

In another embodiment, the system includes a housing connectable to a medium movement sensor. The medium movement sensor generates a movement signal regarding a movement of the medium. The housing is also connectable to an imaging device. The imaging device acquires the internal images upon receiving a control signal having an acquire output. The system further includes a controller secured to the housing. The controller is operable to receive the movement signal, to generate a control signal having an acquire output based on the movement signal, and to provide the control signal having an acquire output to the imaging device.

In another embodiment the invention provides a method of acquiring a plurality of images of a patient. The method includes determining when a contrast medium is entering the patient, generating an acquire output when the contrast medium enters the patient, providing the acquire output to an imaging device, and acquiring the plurality of images with the imaging device upon receiving the acquire output. Other features and advantages of the invention will become apparent by consideration of the detailed description and accompanying drawings.

DETAILED DESCRIPTION

Before any embodiments of the invention are explained, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
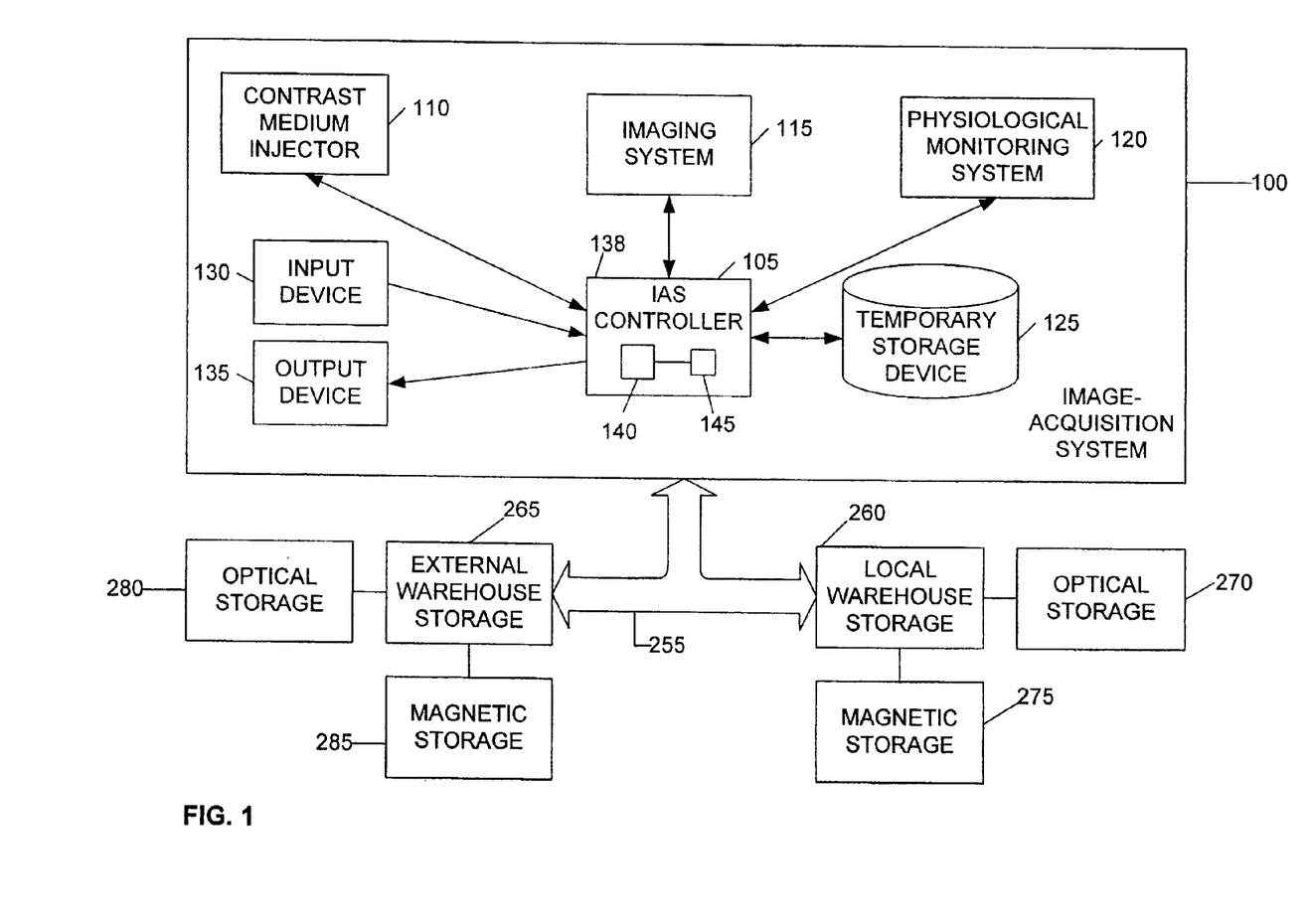
FIG. 1 is a schematic diagram of a system embodying the invention for acquiring a plurality of images of a patient.

A system 100 for acquiring a plurality of images of a patient (also referred to as an "image-acquisition system") is schematically shown in FIG. 1. An example image-acquisition system 100 is a cath-lab, or a portion of a cath-lab.

As shown in FIG. 1, the image-acquisition system 100 generally includes an image-acquisition system (IAS) controller 105, a contrast medium injector 110, an imaging system 115, a physiological monitoring system 120, one or more temporary storage devices 125, one or more input devices 130, and one or more output devices 135. As will become apparent below, one or more components of the image-acquisition system 100 may not be required for all embodiments. For example, in some embodiments, the monitoring system 120 may not be required. Furthermore, one or more components of the image-acquisition system 100 may be combined. For example, the functions of the IAS controller 105, the one or more input devices 130, and the one or more output devices 135, may be incorporated within the injector 110, the imaging system 115 and/or the monitoring system 120. Unless specified otherwise, for simplifying the description below, it will be assumed that the image-acquisition system 100 includes each of the components shown in FIG. 1 and is configured as schematically shown.

As shown in FIG. 1, the IAS controller 105 includes a housing 138 that secures or holds a processing unit 140 and a memory 145. The memory 145 includes one or more software modules having instructions, and the processing unit 140 retrieves, interprets, and executes the instructions of the one or more software modules to control the image-acquisition system 100. For example, the processing unit 140 may include an Intel Pentium brand microprocessor capable of executing a plurality of instructions. However, other microprocessors and microcontrollers may be used with the invention. In addition, the processing unit 140 may be constructed with other analog and/or digital logic circuitry, and may include integrated and/or discrete circuit elements. Also, the IAS controller 105 may include other elements (e.g., one or more analog-to-digital converters, one or more drivers, one or more power supplies, etc.) that would be apparent to one skilled in the art to control or support the IAS controller 105.

In general, for the embodiment shown, the software modules stored within the memory 145 instruct the processing unit 140 to receive signals or inputs from the injector 110, the imaging system 115, the monitoring system 120 and the input device 130, to analyze the received inputs, and to provide signals having data or outputs to the injector 110, the imaging system 115, the monitoring system 120, and the output device 135.

In other embodiments not shown, the IAS controller 105 may directly communicate with any element of the injector 110, the imaging system 115, and/or the monitoring system 120. For example, the IAS controller 105 may directly communicate with a medium movement sensor (discussed below) of the injector 110, or may directly communicate with an imaging device (discussed below) of the imaging system 115. This is even more apparent if the functions of the IAS controller 105 is incorporated within the injector 110, the imaging system 115 and/or the monitoring system 120. The operation and control of the image-acquisition system 100 is discussed in more detail below.

Figure 2:
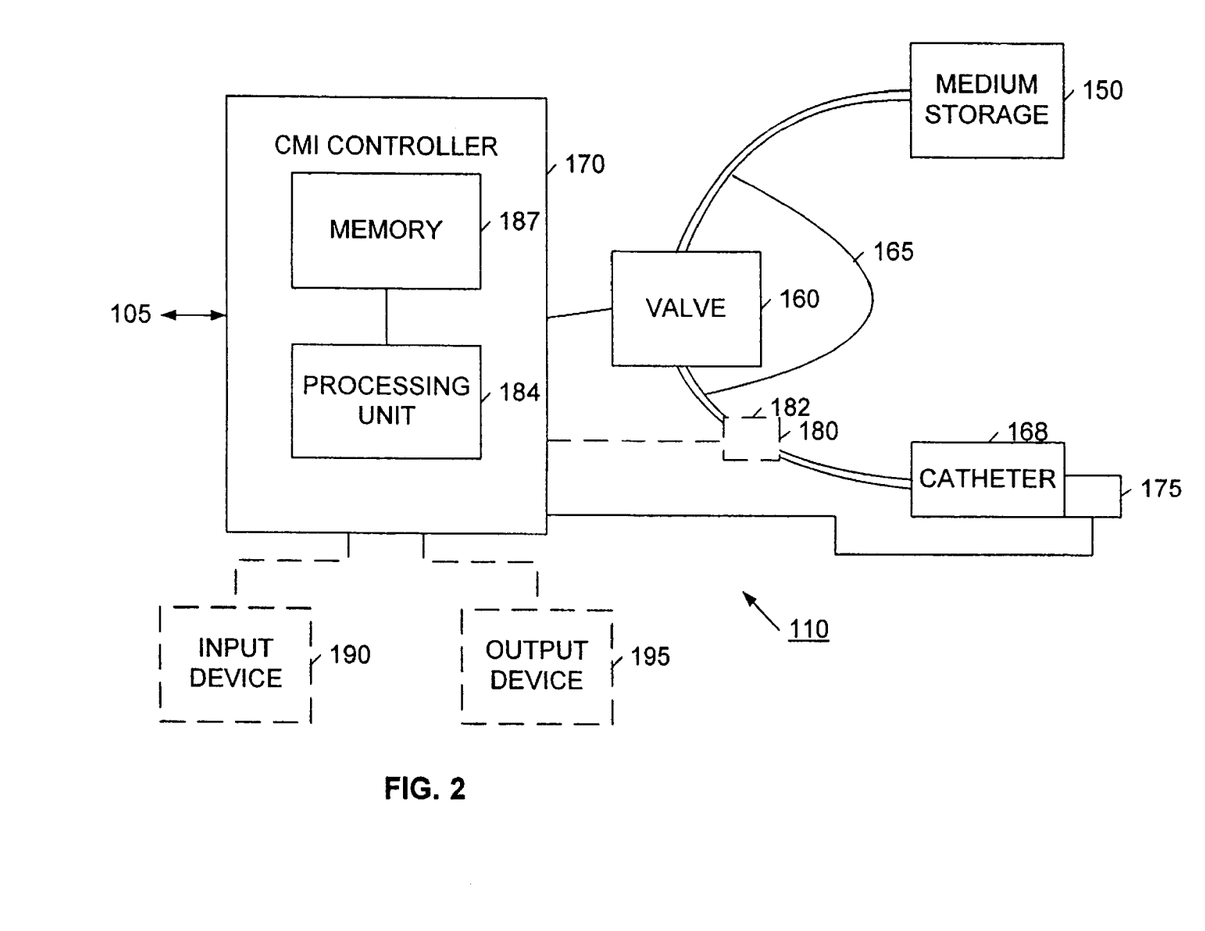
FIG. 2 is a schematic diagram of a contrast medium injector used in the image-acquisition system.

The contrast medium injector 110 is connected to the IAS controller 105. As used herein, the term "connection," and variations thereof (e.g., connect, connected, connecting, etc.), includes direct and indirect connections. The connection, unless specified, may be by mechanical, electrical, chemical, and/or electro-magnetic means, or any combination of the foregoing (e.g. electro-mechanical). As schematically shown in FIG. 2, the injector 110 includes a medium storage 150, a valve 160, a tubing system 165, a catheter 168, a contrast medium injector (CMI) controller 170, and one or more sensors 175 and 180. The medium storage 150 stores a contrast medium for injection within the patient. The medium is a substance used to increase the contrast of the images acquired by the image-acquisition system 100. The valve 160 is connected to the medium storage 150 by the tubing system 165, and controls the movement of the contrast medium through the tubing system 165. The injector 110 may also include a pump (not shown) for moving the medium through the tubing system. The control of the valve is by a control signal transmitted from the CMI controller 170. When the valve 160 is open, the contrast medium is provided to the catheter 168. The catheter 168, which is inserted within the patient, provides the photogenic medium into the patient. The movement of the contrast medium from the medium storage to the catheter is well known in the art and will not be discussed in further detail.

In the embodiment shown, the contrast medium injector 110 further includes a sensor 175 (e.g., a thermal sensor, a flow sensor, etc.) that provides a movement signal to the CMI controller 170. The sensor 175 is attached to the catheter 168 such that the sensor 175 provides a "detect" output within the movement signal when the medium is being inserted within the patient. In addition or in alternative to the sensor 175, the injector 110 may include other sensors located between the medium storage and the catheter 168 (e.g., sensor 180). The sensor 180 (shown in phantom at location 182) provides a second movement signal, and generates a second detect output that informs the CMI controller 170 when the contrast medium passes location 182. The sensors 175 and 180 provide information to the CMI controller regarding the movement of the contrast medium within the injector 110. Additionally, it is envisioned that, in other embodiments, the sensors 175 and 180 may be directly connected to the IAS controller 105, and directly communicate the movement signals to the IAS controller 105. It is also envisioned that the sensors 175 and 180 may not be required. For those embodiments, either the CMI controller 170 or the IAS controller 105 generates an expected location of the contrast medium in response to the opening of the valve 160. For example, the IAS controller 105 may use a contrast medium flow rate to predict a location of the medium upon the CMI controller opening the valve 160.

The CMI controller 170 includes a processing unit 184 and a memory 187. The memory 187 includes one or more software modules having instructions, and the processing unit 184 retrieves, interprets, and executes the instructions of the one or more software modules to control the injector 110. For example, the processing unit 184 may include an Intel Pentium brand microprocessor capable of executing a plurality of instructions. However, other microprocessors and microcontrollers may be used with the invention. In addition, the processing unit 184 may alternatively be constructed with other analog and/or digital logic circuitry, and may include integrated and/or discrete circuit elements.

In general, for the embodiment shown, the software modules stored within the memory 187 instruct the processing unit 184 to receive signals or inputs from sensors 175 and 180 and the IAS controller 105, to analyze the received inputs, and to provide signals having outputs to the valve 160 and the IAS controller 105. Also, it is envisioned that one or more functions performed by the CMI controller 170 may be performed by the IAS controller 105.

The CMI Injector 110 may further include one or more input devices 190 and one or more output devices 195 (shown in phantom). The one or more input devices 190 provide an interface allowing an operator (e.g., a technician, a doctor, a nurse, etc.) to manually control the injector 110. Example input devices 190 include knobs (including trim knobs), dials (including wheels), push buttons (including keyboards, keypads, etc.), switches, pedals, touch devices (including touch screens), pointing devices (including mouses, trackballs, etc.), and other similar input devices. The one or more output devices 195 provide an interface between the injector 110 and the operator, and allow the injector 110 to provide outputs to the operator. Example output devices 195 include display lights (including light-emitting diodes, incandescent bulbs, discharge lamps, fluorescent bulbs, etc.), display screens (including CRTs, touch screens, LCDs, etc.), sound devices (including speakers, tone generating devices, buzzers, etc.) data storage devices (including magnetic storage devices and optical storage devices, etc.), and hard copy devices (including printers, plotters, etc.).

Figure 3:
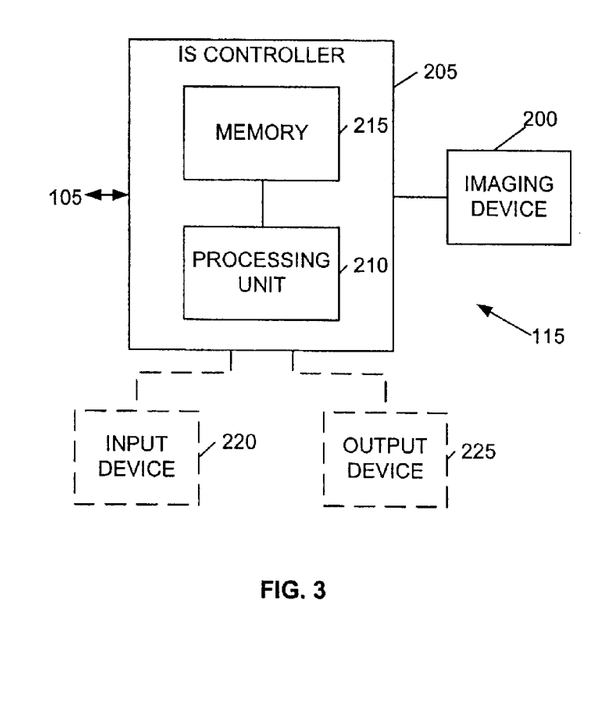
FIG. 3 is a schematic diagram of an imaging system used in the image-acquisition system.

As shown in FIG. 1, the imaging system 115 is connected to the controller 105. As schematically shown in FIG. 3, the imaging system 115 includes an imaging device 200 operable to generate internal images of a patient, and an imaging system (IS) controller 205. For example, the imaging system 115 may be an x-ray system, and the imaging device 200 may include a tube that emits x-rays, a detector that receives x-rays, an image intensifier that intensifies the received x-rays, a digital converter or camera, and a video stream or output. The imaging device is well known in the art and will not be discussed in further detail.

The IS controller 205 includes a processing unit 210 and a memory 215. The memory 215 includes one or more software modules having instructions, and the processing unit 210 retrieves, interprets, and executes the instructions of the one or more software modules to control the imaging system 115. For example, the processing unit 210 may include an Intel Pentium brand microprocessor capable of executing a plurality of instructions. However, other microprocessors and microcontrollers may be used with the invention. In addition, the processing unit 210 may alternatively be constructed with other analog and/or digital logic circuitry, and may include integrated and/or discrete circuit elements.

In general, and for the embodiment shown, the software modules stored within the memory 215 instruct the processing unit 210 to receive signals or inputs from the IS controller 205, to receive the video stream from the imaging device 200, to analyze the received inputs, to process the video stream, to provide signals having outputs to the IAS controller 105, and to provide the processed video stream or image files to the IAS controller. Also, it is envisioned that one or more functions performed by the IS controller 205 may be performed by the IAS controller 105.

The imaging system 110 may further include one or more input devices 220 and one or more output devices 225 (shown in phantom). The one or more input devices 220 provide an interface allowing an operator (e.g., a technician, a doctor, a nurse, etc.) to manually control the imaging system 115. Example input devices 220 include knobs (including trim knobs), dials (including wheels), push buttons (including keyboards, keypads, etc.), switches, pedals, touch devices (including touch screens), pointing devices (including mouses, trackballs, etc.), and other similar input devices. The one or more output devices 225 provide an interface between the imaging system 115 and the operator, and allow the imaging system 115 to provide outputs to the operator. Example output devices 225 include display lights (including light-emitting diodes, incandescent bulbs, discharge lamps, fluorescent bulbs, etc.), display screens (including CRTs, touch screens, LCDs, etc.), sound devices (including speakers, tone generating devices, buzzers, etc.) data storage devices (including magnetic storage devices and optical storage devices, etc.), and hard copy devices (including printers, plotters, etc.).

As shown in FIG. 1, the physiological monitoring system 120 is connected to the IAS controller 105. As used herein, the term physiological monitoring system means any system that obtains at least one physiological signal from the patient. For example, the monitoring system 120 may be a hemodynamic monitoring system, a patient monitor, an electrocardiograph, or similar device.

The monitoring system 120 provides additional information to the IAS controller 105 regarding the patient. For example, the monitoring system 120 may provide the patient's heart rate and/or ventricular ejection fraction to predict how fast the contrast medium will diffuse through the patient and region of interest. Based on the rate, pressure and ECG, the IAS controller 105 may determine an optimal time to start or stop the movement of the medium. Additionally, the monitoring system may inform the IAS controller of an emergency, which results in the IAS controller closing the valve 160.

Figure 4:
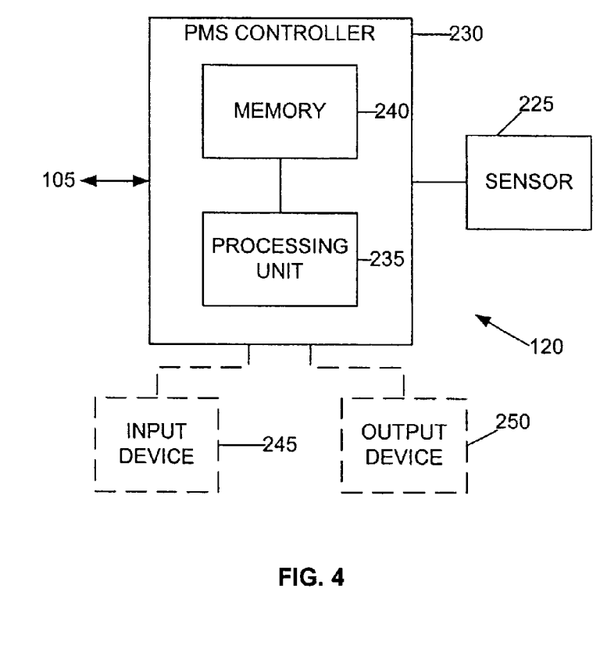
FIG. 4 is a schematic diagram of a physiological monitoring system used in the image-acquisition system.

As schematically shown in FIG. 4, the monitoring system 230 includes one or more sensors 225 (e.g., blood pressure sensors, electrodes, catheters, etc.) connectable to the patient, and a physiological monitor system (PMS) controller 230.

The PMS controller 230 includes a processing unit 235 and a memory 240. The memory 240 includes one or more software modules having instructions, and the processing unit 235 retrieves, interprets, and executes the instructions of the one or more software modules to control the physiological monitoring system 230. For example, the processing unit 235 may include an Intel Pentium brand microprocessor capable of executing a plurality of instructions. However, other microprocessors and microcontrollers may be used with the invention. In addition, the processing unit 235 may alternatively be constructed with other analog and/or digital logic circuitry, and may include integrated and/or discrete circuit elements. In general, for the embodiment shown, the software modules stored within the memory 240 instruct the processing unit 235 to receive signals or inputs from the IAS controller 105, receive one or more physiological signals from the patient via the sensor 225, analyze the received inputs, process the one or more physiological signals, provide signals having outputs to the IAS controller 105, and provide the one or more processed physiological signals to the IAS controller 105. Also, it is envisioned that one or more functions performed by the PMS controller 230 may be performed by the IAS controller 105.

The physiological monitoring system 120 may further include one or more input devices 245 and one or more output devices 250 (shown in phantom). The one or more input devices provide 245 an interface allowing an operator (e.g., a technician, a doctor, a nurse, etc.) to manually control the physiological monitoring system 230. Example input devices 245 include knobs (including trim knobs), dials (including wheels), push buttons (including keyboards, keypads, etc.), switches, pedals, touch devices (including touch screens), pointing devices (including mouses, trackballs, etc.), and other similar input devices. The one or more output devices 250 provide an interface between the physiological monitoring system 230 and the operator, and allow the monitoring system 230 to provide outputs to the operator. Example output devices 195 include display lights (including light-emitting diodes, incandescent bulbs, discharge lamps, fluorescent bulbs, etc.), display screens (including touch screens, LCDs, etc.), sound devices (including speakers, tone generating devices, buzzers, etc.), data storage devices (including magnetic and optical storage devices), and hard copy devices (including printers).

As shown in FIG. 1, the image-acquisition system 100 includes one or more input devices 130. The one or more input devices provide an interface allowing an operator (e.g., a technician, a doctor, a nurse, etc.) to manually control the image-acquisition system. For the embodiment shown and unless specified otherwise, the operator can manually control the injector 110, the imaging system 115, the monitoring system 120, and the IAS controller 105 with the one or more input devices 130. For example, the operator may provide a "start" input that results in the injector 110 opening the valve 160 for inserting the contrast medium within the patient. Example input devices 190 include knobs (including trim knobs), dials (including wheels), push buttons (including keyboards, keypads, etc.), switches, pedals, touch devices (including touch screens), pointing devices (including mouses, trackballs, etc.), and other similar input devices.

The image acquisition system 100 further includes one or more output devices 135. The one or more output devices 195 provide an interface between the image-acquisition system 110 and the operator, and allow the image-acquisition system 110 to provide outputs to the operator. Example output devices 195 include display lights (including light-emitting diodes, incandescent bulbs, discharge lamps, fluorescent bulbs, etc.), display screens (including touch screens, LCDs, etc.), sound devices (including speakers, tone generating devices, buzzers, etc.), data storage devices (including magnetic storage devices, optical storage devices, etc.), hard copy devices (including printers), and one or more network connections. For the embodiment shown, the image-acquisition system 100 includes a separate temporary storage device 125, and a network connection 255 for connecting the image-acquisition system 100 to a local warehouse storage 260 and/or an external warehouse storage 265. The local and external warehouse storage 260 and 265 may include optical and/or magnetic storage devices 270, 275, 280 and/or 285, respectively. While performing one or more acquisition loops, the image-acquisition system 100 temporarily stores the acquired images at the temporary storage device 125. Upon completing the case, the operator may store the acquired images and related data in a storage device at the one or more output devices 135, or may transmit the images and data to the local and/or external warehouse storage 260 and/or 265.

Having described the image-acquisition system 100, the operation will know be described. Unless specified otherwise, the operation description below is for the embodiment shown in the figures. It is envisioned that the operation may be modified for other embodiments. For example, if the monitoring system 120 is not present, then the operation description below for the monitoring system 120 does not apply. Furthermore, even if all of the components of the image-acquisition system 100 shown are present, for some embodiments, it is envisioned that not all of the acts below may be required, that some of the acts may be modified, or that the order of the acts may vary.

In operation, a patient lies on a table and the image-acquisition system 100 is set into place as is known in the art. For example, the contrast medium sensors 175 and 180 are attached to the injector 110 (if necessary), the catheter 168 is inserted within the patient, the monitoring sensors 225 are placed on the patient, and the imaging device 200 is properly placed into position. While inserting the catheter 168 within the patient, the imaging system 115 may be in a low-resolution or fluoro mode for assisting catheter placement. After properly setting the image-acquisition system, a technician enters a "begin" input to the input device 130. The "begin" input is transmitted from the IAS controller 105 to the injector 110. The "begin" input results in a valve control output that opens the valve 165, allowing the contrast median to move towards the catheter for injection to the patient. While the median proceeds towards injection, the contrast medium sensors 175 and 180 transmit monitoring signals, respectively, to the CMI controller 170. For example, the first monitoring sensor 175 provides a first monitoring signal to the CMI controller 170, and the second monitoring sensor 180 (if present) provides a second monitoring signal to the CMI controller. The monitoring sensors 175 and 180 generate "detect" outputs, respectively, when the median passes the sensors 175 and 180. For example, the first monitoring sensor 175 produces a first "detect" output when the medium passes the first sensor 175, and the second monitoring sensor 175 produces a second "detect" output when the medium passes the second sensor 175. The monitoring signals may be processed by the processing unit 184 or may be transmitted as acquired to the IAS controller 105 for processing.

Upon receiving the first "detect" output, the IAS controller 105 generates an "activate" output that is communicated to the imaging system 115. The "activate" output informs the imaging system 115 to "warm-up" the imaging device 200 for acquisition. Although, the imaging system 115 may be already acquiring low-quality images, the imaging system may need to perform further steps or functions in order to acquire high-quality images (i.e., images for diagnosis). For example, if the imaging system is a x-ray system, then the output of the x-ray tube may need to be increased to acquire high-quality images.

Upon receiving the second "detect" output, the IS controller 105 generates an "acquire" output that is communicated to the imaging system 115. The "acquire" output results in the imaging system 115 acquiring or recording the high-resolution images until a "cease" output is provided from the IAS controller 105 to the imaging system 115. For generating the "cease" output, the IAS controller 105 analyzes the one or more physiological signals (e.g., the patient's heart rate, the patient's blood pressure, etc.) acquired by the monitoring system 120 to predict when the contrast medium will be too diluted to produce useful images. Alternatively, the IAS controller may generate the "cease" output if an error or problem arises (e.g., the patient goes into cardiac arrest). The "cease" output ends the acquisition mode and "deactivates" the imaging device 200. Additionally, the "cease" output may result in the CMI controller closing the valve 160, which prevents further contrast medium from injecting into the patient.

Similar to above, deactivating the imaging device 200 may only change the modes of the imaging system from high-resolution mode to low-resolution mode. After acquiring the high-resolution images, the images are provided to the IAS controller 105 and are temporarily stored in the temporary storage device 125.

After completing the first loop, the image-acquisition system 100 may perform addition loops on the patient. The image acquisition system 100 typically stores the loops at the temporary storage device 125 until the test is complete. Upon completing the test, the resulting images and test data (e.g., patient demographics, test event log, etc.) may be provided to the one or more output devices 135, and/or may be transmitted to the internal and/or external warehouse storage 260 or 265. Alternatively, the IAS may transmit the resulting images and test data when each loop is complete.

As was stated above, it is envisioned that other methods of operations are possible with the invention. For example, if the monitoring sensors 175 and 180 are directly connected to the IAS controller 105, the technician may enter the begin input directly to the CMI controller 170, and the monitoring sensors may provide the monitoring signal directly to the IAS controller 105. The IAS controller 105 determines that the test is in progress when it receives the second detect output from the monitoring sensor 180, and controls the imaging system as is described above.

In another embodiment, if the CMI controller does not include any monitoring sensors 175 or 180, then the CMI controller 170 or IAS controller 105 predicts an expected location of the contrast medium within the tubing system 165. For example, when the CMI controller 170 opens the valve 160, it provides an output regarding the status of the valve to the IAS controller 105. In response, the IAS controller 105 produces the expected location of the medium using a timer and a known fluid-flow dynamic rate of the contrast medium within the tubing system 165. Additionally, for other embodiments, where the IAS controller is incorporated within the injector 110, imaging system 115, and/or monitoring system 120, the operation of the system 100 may be modified accordingly.

As is apparent from the description above, the invention provides, among other things, a useful system for acquiring a plurality of images of a patient, and a controller for operating the same. Various features and advantages of the invention are set forth in the following claims.

What is claimed is:

1. A system for acquiring a plurality of internal images of a patient, the system comprising:
a contrast medium injector operable to introduce a contrast medium into the patient, and to generate a movement signal relating to movement of the medium;
a controller in communication with the injector, the controller being operable to receive the movement signal, and to generate a control signal having an acquire output based on the movement signal; and
an imaging system having an imaging device that acquires internal images of the patient, the imaging system being operable to receive the control signal and to acquire the plurality of internal images in response to receiving the acquire output.

2. A system as set forth in claim 1 wherein the injector includes a medium movement sensor that generates the movement signal.

3. A system as set forth in claim 2 wherein the injector includes a catheter insertable within the patient, wherein the sensor is connected to the catheter, and wherein the movement signal includes a detect output signifying the medium passing through the catheter.

4. A system as set forth in claim 3 wherein the controller generates the acquire output upon receiving the detect output.

5. A system as set forth in claim 2 wherein the injector includes a catheter insertable within the patient and a tubing system having a valve, the tubing system being connected to the catheter, wherein the sensor is connected to the tubing system at a location, and wherein the movement signal includes a detect output signifying the medium passing through the location where the sensor is connected to the tubing system.

6. A system as set forth in claim 5 wherein the controller generates the acquire output at a delay after receiving the detect output.

7. A system as set forth in claim 2 wherein the injector includes a second medium movement sensor for generating a second movement signal regarding a movement of the medium, wherein the controller is in communication with the second sensor, and wherein the controller receives the second movement signal and generates an activate output in the control signal based on the second movement signal.

8. A system as set forth in claim 7 wherein the imaging device includes a tube, and wherein the imaging system activates the tube in response to receiving the activate output.

9. A system as set forth in claim 7 wherein the injector includes a catheter insertable within the patient and a tubing system having a valve, the tubing system being connected to the catheter, wherein the first sensor is connected to the catheter, wherein the first movement signal includes a first detect signal signifying the medium passing through the catheter, wherein the second sensor is connected to the tubing system at a location, wherein the second movement signal includes a second detect output signifying the medium passing through the location where the sensor is connected to the tubing system.

10. A system as set forth in claim 9 wherein the controller generates the activate output upon receiving the second detect output, and wherein the controller generates the acquire output upon receiving the first detect output.

11. A system as set forth in claim 10 wherein the imaging device includes a tube, and wherein the imaging system activates the tube in response to receiving the activate output.

12. A system as set forth in claim 1 wherein the plurality of images are digital images, and the system further comprises a digital storage device for storing the plurality of images.

13. A system as set forth in claim 1 wherein the imaging device includes a tube that emits radiation, a detector that receives the radiation and converts the radiation into the plurality of images, and a video stream that transmits the plurality of images.

14. A system as set forth in claim 13 wherein the imaging system is an x-ray system, and the tube is an x-ray tube.

15. A system as set forth in claim 1 wherein the imaging system includes the controller.

16. A system as set forth in claim 1 wherein the injector includes the controller.

17. A system as set forth in claim 1 wherein the controller is in communication with the injector and the imaging system.

18. A system as set forth in claim 1 wherein the system further comprises a patient monitor that generates a monitor signal regarding a physiological condition of the patient, wherein the controller is in communication with the monitor, and wherein the controller receives the monitor signal and generates the control signal having a cease output based in part on the monitor signal.

19. A system as set forth in claim 18 wherein the imaging system ceases acquiring the plurality of internal images in response to receiving the cease output.

20. A system as set forth in claim 18 wherein the patient monitor is a hemodynamic monitoring system.

21. A system for acquiring a plurality of images of a patient comprising:
a housing connectable to a medium movement sensor that generates a movement signal regarding a movement of a medium, and to an imaging device that acquires the images upon receiving a control signal having an acquire output; and
a controller secured to the housing, the controller being operable to receive the movement signal, to generate the control signal having an acquire output based on the movement signal, and to communicate the control signal having an acquire output to the imaging device.

22. A system as set forth in claim 21 wherein the system further comprises a contrast medium injector, and wherein the contrast medium injector includes the housing.

23. A system as set forth in claim 22 wherein the system further comprises an imaging system having the imaging device, and wherein the housing is connected to the imaging system.

24. A system as set forth in claim 23 wherein the system further comprises a physiological monitoring system, and wherein the housing is connected to the physiological monitoring system.

25. A system as set forth in claim 22 wherein the system further comprises the medium movement sensor, and wherein the housing is connected to the medium movement sensor.

26. A system as set forth in claim 25 wherein the injector includes the sensor.

27. A system as set forth in claim 21 wherein the system further comprises an imaging system including the imaging device, and wherein the imaging system includes the housing.

28. A system as set forth in claim 27 wherein the system further comprises a medium movement sensor, and wherein the housing is connected to the medium movement sensor.

29. A system as set forth in claim 27 wherein the system further comprises a contrast medium injector operable to introduce the contrast medium within the patient, and wherein the sensor is connected to the injector.

30. A system as set forth in claim 29 wherein the injector includes the sensor.

31. A system as set forth in claim 28 wherein the system further includes a physiological patient monitor, and wherein the housing is connected to the physiological patient monitor.

32. A system as set forth in claim 21 wherein the system further comprises a physiological monitoring device, and wherein the physiological monitoring device includes the housing.

33. A system as set forth in claim 32 wherein the system further comprises an imaging system including the imaging device, and wherein the housing is connected to the imaging device.

34. A system as set forth in claim 33 wherein the system further comprises a medium movement sensor, and wherein the housing is connected to the medium movement sensor.

35. A system as set forth in claim 34 wherein the system further comprises a contrast medium injector operable to introduce the contrast medium within the patient, and wherein the sensor is connected to the injector.

36. A system as set forth in claim 35 wherein the injector includes the sensor.

37. A system as set forth in claim 21 wherein the system further comprises a medium movement sensor and wherein the housing is connected to the medium movement sensor.

38. A system as set forth in claim 37 wherein the system further comprises a contrast medium injector operable to introduce the contrast medium within the patient, and wherein the sensor is connected to the injector.

39. A system as set forth in claim 38 wherein the injector includes the sensor.

40. A system as set forth in claim 39 wherein the injector includes a catheter insertable within the patient, wherein the sensor is connected to the catheter, and wherein the movement signal includes a detect output signifying the medium passing through the catheter.

41. A system as set forth in claim 40 wherein the controller generates the acquire output upon receiving the detect output.

42. A system as set forth in claim 38 wherein the injector includes a catheter insertable within the patient and a tubing system having a valve, the tubing system being connected to the catheter, wherein the sensor is connected to the tubing system at a location, and wherein the movement signal includes a detect output signifying the medium passing through the location where the sensor is connected to the tubing system.

43. A system as set forth in claim 42 wherein the controller generates the acquire output at a delay after receiving the detect output.

44. A system as set forth in claim 37 wherein the system further includes a second medium movement sensor for generating a second movement signal regarding a movement of the medium, wherein the controller is in communication with the second sensor, and wherein the controller receives the second movement signal and generates an activate output in the control signal based on the second movement signal.

45. A system as set forth in claim 44 wherein the system further comprises an imaging system having the imaging device, and wherein the housing is connected to the imaging system.

46. A system as set forth in claim 45 wherein the imaging device includes a tube, and wherein the imaging system activates the tube in response to receiving the activate output.

47. A system as set forth in claim 46 wherein the plurality of images are digital images, and wherein the system further comprises a digital storage device for storing the plurality of images.

48. A system as set forth in claim 46 wherein the system further comprises a contrast medium injector operable to introduce the contrast medium within the patient, and wherein the first and second sensors are connected to the injector.

49. A system as set forth in claim 48 wherein the injector includes a catheter insertable within the patient and a tubing system having a valve, the tubing system being connected to the catheter, wherein the first sensor is connected to the catheter, wherein the first movement signal includes a first detect signal signifying the medium passing through the catheter, and wherein the second sensor is connected to the tubing system at a location, wherein the second movement signal includes a second detect output signifying the medium passing through the location where the sensor is connected to the tubing system.

50. A system as set forth in claim 49 wherein the controller generates the activate output upon receiving the second detect output, and wherein the controller generates the acquire output upon receiving the first detect output.

51. A method of acquiring a plurality of images of a patient, the method comprising:
determining when a contrast medium is entering the patient;
generating an acquire output when the contrast medium enters the patient;
providing the acquire output to an imaging device; and
acquiring the plurality of images with the imaging device upon receiving the acquire output.

52. A method as set forth in claim 51 wherein determining when the contrast medium is entering the patient includes:
attaching a medium movement sensor to a contrast medium injector, and
generating a movement signal with the sensor regarding a movement of the medium within the injector.

53. A method as set forth in claim 52 wherein the contrast medium injector includes a catheter insertable within the patient, wherein attaching a medium movement sensor to the contrast medium injector includes attaching the sensor to the catheter, and wherein generating the movement signal includes generating a detect output signifying the medium passing through the catheter.

54. A method as set forth in claim 53 wherein generating an acquiring output includes generating the acquiring output in response to the generating the detect output.

55. A method as set forth in claim 52 wherein the contrast medium injector includes a catheter insertable within the patient and a tubing system having a valve, wherein attaching a medium movement sensor to the contrast medium injector includes attaching the sensor to the tubing system at a location, and wherein generating the movement signal includes generating a detect output signifying the medium passing through the location where the sensor is connected to the tubing system.

56. A method as set forth in claim 55 wherein generating an acquire output includes generating the acquire output in response to the generating the detect output.

57. A method as set forth in claim 55 wherein the generating the acquire output in response to the generating of the detect output includes generating the acquire output at a delay after generating the detect output.

58. A method as set forth in claim 52 wherein determining when the contrast medium is entering the patient further includes:
attaching a second medium movement sensor to contrast medium indicator, and
generating a second movement signal with the sensor regarding a movement of the medium within the injector.

59. A method as set forth in claim 58 wherein attaching a first medium movement sensor to the contrast medium injector includes attaching the first sensor to the catheter, wherein generating the first movement signal includes generating a first detect output signifying the medium passing through the catheter, wherein attaching the second medium movement sensor to the contrast medium injector includes attaching the second sensor to the tubing system at a location, and wherein generating the second movement signal includes generating a second detect output signifying the medium passing through the location where the sensor is connected to the tubing system.

60. A method as set forth in claim 59 wherein generating an acquire output includes generating the acquire output in response to generating the first detect output, and wherein the method further comprising generating an activate output in response to generating the second detect output.

61. A method as set forth in claim 60 wherein the imaging device includes a tube, and wherein the method further comprises:
providing the activate output to the imaging device; and
activating the tube upon receiving the activating output.

62. A method as set forth in claim 51 wherein the plurality of images are digital images, and wherein the method further comprises storing the acquired plurality of images.

63. A method as set forth in claim 62 wherein the imaging device includes a tube, and wherein the acquiring the plurality of images includes
emitting radiation with the tube,
detecting the radiation,
converting the radiation into a plurality of images,
and streaming the plurality of images.

64. A method as set forth in claim 63 wherein the tube is an x-ray tube.

65. A method as set forth in claim 51 and further comprising:
monitoring a physiological signals of the patient;
generating a cease output based in part on the physiological signal;
providing the cease output to the imaging device;
ceasing the acquiring of the plurality of images with the imaging device upon receiving the cease output.

66. A method as set forth in claim 51 wherein the method further comprises providing a contrast medium injector including a tubing system having a valve, and wherein the determining when a contrast medium is entering the patient includes estimating the location of the medium within the tubing system.

67. A method as set forth in claim 66 wherein estimating the location of the medium includes opening the valve and starting a timer in response to opening the valve.

68. A method of acquiring a plurality of internal images of a patient, the method comprising:
initiating movement of a contrast medium, the medium to enter the patient;
generating a movement signal relating to the movement of the medium;
generating an acquire output based on the movement signal; and
acquiring the plurality of images in response to receiving the acquire output.

69. A method as set forth in claim 68, wherein the act of acquiring includes:
sensing movement of the medium with a medium movement sensor;

generating a detect output in the movement signal when the sensor senses movement of the medium; and generating the acquire output based on the detect output.

70. A method as set forth in claim 68 and further comprising:

attaching a medium movement sensor to a contrast medium injector, and generating the movement signal with the sensor regarding a movement of the medium within the injector.

71. A method as set forth in claim 70 wherein the contrast medium injector includes a catheter insertable within the patient, wherein attaching a medium movement sensor to the contrast medium injector includes attaching the sensor to the catheter, and wherein generating the movement signal includes generating a detect output signifying the medium passing through the catheter.

72. A method as set forth in claim 70 wherein the contrast medium injector includes a catheter insertable within the patient and a tubing system having a valve, wherein attaching a medium movement sensor to the contrast medium injector includes attaching the sensor to the tubing system at a location, and wherein generating the movement signal includes generating a detect output signifying the medium passing through the location where the sensor is connected to the tubing system.

73. A method as set forth in claim 70 wherein determining when the contrast medium is entering the patient further includes:

attaching a second medium movement sensor to contrast medium indicator, and generating a second movement signal with the sensor regarding a movement of the medium within the injector.

74. A method as set forth in claim 73 wherein attaching a first medium movement sensor to the contrast medium injector includes attaching the first sensor to the catheter, wherein generating the first movement signal includes generating a first detect output signifying the medium passing through the catheter, wherein attaching the second medium movement sensor to the contrast medium injector includes attaching the second sensor to the tubing system at a location, and wherein generating the second movement signal includes generating a second detect output signifying the medium passing through the location where the sensor is connected to the tubing system.

75. A method as set forth in claim 68 wherein the plurality of images are digital images, and wherein the method further comprises storing the acquired plurality of images.

76. A method as set forth in claim 75 wherein the acquiring the plurality of images includes emitting radiation, detecting the radiation, converting the radiation into a plurality of images, and streaming the plurality of images.

* * * * *